(12) United States Patent
Shiraishi et al.

(10) Patent No.: US 8,749,787 B2
(45) Date of Patent: Jun. 10, 2014

(54) FLUORESCENCE DETECTING APPARATUS AND FLUORESCENCE DETECTING METHOD

(75) Inventors: Junpei Shiraishi, Kanagawa-ken (JP); Masashi Hakamata, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 293 days.

(21) Appl. No.: 13/045,361

(22) Filed: Mar. 10, 2011

(65) Prior Publication Data
US 2011/0240879 A1 Oct. 6, 2011

(30) Foreign Application Priority Data
Mar. 31, 2010 (JP) .................................. 2010-083897

(51) Int. Cl.
*G01N 21/00* (2006.01)

(52) U.S. Cl.
USPC .... 356/432; 356/445; 250/432 R; 250/363.01

(58) Field of Classification Search
CPC ............ G01N 21/1717; G01N 21/255; G01N 29/2418; G01N 21/1702; G01N 21/171
USPC ..................... 356/432, 445; 250/363.1, 432 R
See application file for complete search history.

(56) References Cited

U.S. PATENT DOCUMENTS

| | | | | |
|---|---|---|---|---|
| 6,137,574 A * | 10/2000 | Hill | ................................ | 356/486 |
| 6,630,680 B2 * | 10/2003 | Hakamata et al. | ......... | 250/458.1 |
| 7,453,564 B2 * | 11/2008 | Rensen et al. | ................ | 356/300 |
| 2003/0189707 A1 * | 10/2003 | Naya et al. | ..................... | 356/445 |
| 2006/0187459 A1 * | 8/2006 | Ok et al. | ........................ | 356/445 |
| 2006/0209309 A1 * | 9/2006 | Feng | .............................. | 356/512 |
| 2007/0008536 A1 | 1/2007 | Mitani et al. | | |
| 2008/0117421 A1 * | 5/2008 | Yamaguchi et al. | .......... | 356/417 |
| 2008/0218860 A1 * | 9/2008 | Robertson | ..................... | 359/534 |
| 2009/0321661 A1 | 12/2009 | Ohtsuka | | |

FOREIGN PATENT DOCUMENTS

| | | |
|---|---|---|
| JP | H 03-51761 A | 3/1991 |
| JP | 10-239233 A | 9/1998 |
| JP | 2007-232613 A | 9/2007 |
| JP | 2009-128152 A | 6/2009 |
| JP | 2010-008263 A | 1/2010 |
| WO | WO 2005/088280 A1 | 9/2005 |

OTHER PUBLICATIONS

Notification of Grounds for Rejection, dated Aug. 13, 2013 with partial English translation.

* cited by examiner

*Primary Examiner* — Tarifur Chowdhury
*Assistant Examiner* — Isiaka Akanbi
(74) *Attorney, Agent, or Firm* — McGinn IP Law Group, PLLC (57) ABSTRACT

Excitation light beam is irradiated onto a test region while shifting the irradiation position thereof, when performing analysis of a target substance using an analysis chip having the test region within a flow channel through which a sample solution is caused to flow, for capturing the target substance within the sample solution. Fluorescence generated at the test region is detected as a plurality of adjustment fluorescence signals. The target substance is analyzed using fluorescence generated when the excitation light beam is irradiated at an irradiation position within the test region determined based on the plurality of adjustment fluorescence signals.

16 Claims, 10 Drawing Sheets

FLUORESCENCE DETECTING APPARATUS AND FLUORESCENCE DETECTING METHOD

BACKGROUND OF THE INVENTION

1. Field of the Invention

The present invention is related to a fluorescence detecting apparatus and a fluorescence detecting method for quantitatively or qualitatively analyzing target substances within samples.

2. Description of the Related Art

Plasmon sensors that quantitatively analyze substances within samples using the principle of the surface plasmon resonance phenomenon employing evanescent waves are known (refer to Japanese Unexamined Patent Publication No. 10 (1998)-239233, for example). Japanese Unexamined Patent Publication No. 10 (1998)-239233 discloses that a light beam is irradiated onto the interface between a prism and a metal film, formed on a surface of the prism, that contacts a sample at a total reflection angle. The reflection angle of the light beam which is totally reflected at the interface is detected, to quantitatively analyze a substance within the sample. Further, this patent document discloses that a light source and a light detecting unit are movable, such that samples contained in a plurality of sample containers can be quantitatively analyzed.

In addition, fluorescence detecting apparatus that utilize the aforementioned evanescent waves have also been proposed (refer to Japanese Unexamined Patent Publication No. 2009-128152, for example). Japanese Unexamined Patent Publication No. 2009-128152 discloses that a detection target substance is quantitatively analyzed by detecting fluorescence which is generated when the detection target substance, which is labeled by fluorescent labels, within a sample container is excited by evanescent waves. Further, this patent document discloses that a light source is movable in order to enable adjustment of incident angles with respect to a metal film.

In the fluorescence detecting apparatus disclosed in Japanese Unexamined Patent Publication No. 2009-128152, a micro flow channel, through which a sample is caused to flow, and the metal film are provided in an analysis chip. Different analysis chips are employed for different samples, and the analysis chips are discarded after use. The analysis chips are produced to be of a predetermined size. However, there are cases in which dimensional shifts occur due to manufacturing errors. There is a possibility that the irradiation position of an excitation light beam and the position of the metal film will be shifted due to these dimensional shifts, leading to variations in the intensities of detected fluorescence. As a result, there is a possibility that the accuracy of analysis will deteriorate. Similarly, there are individual differences among apparatuses in the irradiation position of the excitation light beam due to manufacturing errors. Thus, there is a problem that the accuracy of analysis will deteriorate.

SUMMARY OF THE INVENTION

The present invention has been developed in view of the foregoing circumstances. It is an object of the present invention to provide a fluorescence detecting apparatus and a fluorescence detecting method that prevents deterioration in the accuracy of analysis caused by individual differences among analysis chips and apparatuses.

A fluorescence detecting apparatus of the present invention employs an analysis chip having a test region, for capturing a detection target substance included in a sample solution, within a flow channel through which the sample solution is caused to flow, irradiates an excitation light beam onto the test region, and detects fluorescence generated at the test region, to analyze the detection targets substance, and is characterized by comprising:

light irradiating means, for emitting the excitation light beam onto the test region;

fluorescence detecting means, for detecting the fluorescence generated at the test region due to the irradiation of the excitation light beam;

irradiation position adjusting means, for adjusting the irradiation position of the excitation light beam with respect to the test region; and irradiation position control means, for determining the irradiation position of the excitation light beam with respect to the test region during analysis of the detection target substance, based on a plurality of adjustment fluorescence signals detected by the fluorescence detecting means when the irradiation position adjusting means is driven to irradiate the excitation light beam onto the test region while shifting the irradiation position thereof.

A fluorescence detecting method of the present invention employs an analysis chip having a test region within a flow channel through which a sample solution is caused to flow, for capturing a detection target substance included in the sample solution, irradiates an excitation light beam onto the test region, and detects fluorescence generated at the test region, to analyze the detection targets substance, and is characterized by comprising:

emitting the excitation light beam onto the test region;

detecting the fluorescence generated at the test region due to the irradiation of the excitation light beam;

adjusting the irradiation position of the excitation light beam with respect to the test region; and determining the irradiation position of the excitation light beam with respect to the test region during analysis of the detection target substance, based on a plurality of detected adjustment fluorescence signals when the excitation light beam is irradiated onto the test region while shifting the irradiation position thereof.

Here, the detection target substance to be analyzed by the fluorescence detecting apparatus is not limited. Examples of detection target substances include: whole blood; plasma extracted from whole blood by centrifugal separation; and urine. The sample liquid may be that in which the detection target substance and fluorescent labels are mixed. In this case, the test region captures the detection target substance which has bound to the fluorescent labels.

The analysis chip is provided with the test region within the flow channel thereof. It is preferable for the analysis chip to be equipped with a control region that generates fluorescence when the sample solution passes therethrough due to irradiation of the excitation light beam, downstream of the test region. The test region and the control region may be formed by dielectric plates and metal films, for example, and generate electric field enhancing fields when irradiated by the excitation light beam. The fluorescence detecting means may detect fluorescence generated by the detection target substance or the fluorescent labels by being excited by the electric field enhancing field.

The light irradiating means may have a light source for emitting the excitation light beam, and an optical system for causing the excitation light beam emitted by the light source to enter the test region. In this case, the irradiation position adjusting means adjusts the irradiation position of the excitation light beam by moving the position of the optical system with respect to the light source.

The irradiation position control means may determine an irradiation position at which the adjustment fluorescence signal is the greatest from among the plurality of adjustment fluorescence signals as the irradiation position of the excitation light beam. Alternatively, the irradiation position control means may specify a range of irradiation positions in which adjustment fluorescent signals of an intensity which is a predetermined percentage of the greatest adjustment fluorescence signal are obtained, and determines a midpoint position within the specified range of irradiation positions as the irradiation position during an analysis operation.

It is preferable for the irradiation position control means to perform adjustment of the irradiation position each time that the analysis chip is exchanged.

The fluorescence detecting apparatus may further comprise a scanning means for scanning the light irradiation means between the test region and the control region when irradiating the excitation light beam to analyze the detection target substance. Alternatively, a light irradiating means may be provided for each of the test region and the control region.

The fluorescence detecting means may detect the plurality of adjustment fluorescence signals while shifting the irradiation position of the excitation light beam with respect to the test region by scanning performed by the scanning means. In this case, the position control means determines the irradiation position of the excitation light beam in the scanning direction based on the plurality of adjustment fluorescence signals, and determines the irradiation position of the excitation light beam in a direction perpendicular to the flow channel by the irradiation position adjusting means.

The fluorescence detecting apparatus and the fluorescence detecting method of the present invention employs the analysis chip having the test region, for capturing a detection target substance included in a sample solution, within a flow channel through which the sample solution is caused to flow, irradiates an excitation light beam onto the test region, and detects fluorescence generated at the test region, to analyze the detection targets substance. A plurality of adjustment fluorescence signals are detected by the fluorescence detecting means when the irradiation position adjusting means is driven to irradiate the excitation light beam onto the test region while shifting the irradiation position thereof. The irradiation position of the excitation light beam with respect to the test region during analysis of the detection target substance is determined, based on the plurality of detected adjustment fluorescence signals. The detection target substance is analyzed by irradiating the excitation light beam onto the determined irradiation position and detecting fluorescence. Thereby, shifts in the irradiation position of the excitation light beam with respect to test regions due to individual differences among analysis chips and apparatuses are automatically adjusted for. This enables analysis to be performed under the same excitation light beam irradiation conditions for all analysis chips. Therefore, deterioration in the accuracy of analysis due to individual differences among analysis chips can be prevented.

Note that the irradiation position control means may determine an irradiation position at which the adjustment fluorescence signal is the greatest from among the plurality of adjustment fluorescence signals as the irradiation position during an analysis operation. In this case, an irradiation position that yields accurate analysis results can be determined.

Alternatively, the irradiation position control means may specify a range of irradiation positions in which adjustment fluorescent signals of an intensity which is a predetermined percentage of the greatest adjustment fluorescence signal are obtained, and determine a midpoint position within the specified range of irradiation positions as the irradiation position during an analysis operation. In this case as well, an irradiation position that yields accurate analysis results can be determined.

The analysis chip may be equipped with a control region that generates fluorescence when the sample solution passes therethrough due to irradiation of the excitation light beam, downstream of the test region. Scanning means for scanning the light irradiation means between the test region and the control region when irradiating the excitation light beam to analyze the detection target substance may be provided. In this case, the necessity to provide light irradiating means for each of the test region and the control region is obviated, and the structure of the apparatus may be simplified.

Further, the fluorescence detecting apparatus may further comprise a scanning means for scanning the light irradiation means between the test region and the control region when irradiating the excitation light beam to analyze the detection target substance, and the position control means may determine the irradiation position of the excitation light beam in the scanning direction based on the plurality of adjustment fluorescence signals, and may determine the irradiation position of the excitation light beam in a direction perpendicular to the flow channel by the irradiation position adjusting means. In this case, analysis can be performed at an optimal irradiation position, even in the case that positional fluctuations of the test region are present both in the scanning direction and the direction perpendicular thereto due to individual differences among analysis chips.

The test region may be equipped with a dielectric plate and a metal film such that an electric field enhancing field is generated by irradiation of the excitation light beam, and the detection target substance may generate fluorescence by being excited by the electric field enhancing field. In this case, the intensity of the electric field enhancing field being different for each analysis chip can be prevented, and accurate analysis of the detection target substance is enabled.

DESCRIPTION OF THE PREFERRED EMBODIMENTS

Figure 1:
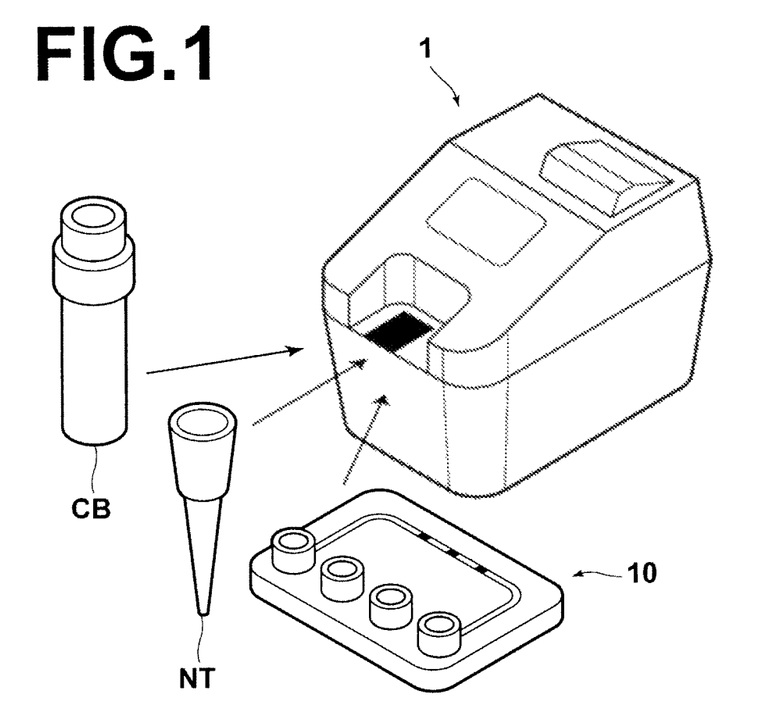
FIG. 1 is a diagram that schematically illustrates a fluorescence detecting apparatus according to a preferred embodiment of the present invention.

Hereinafter, embodiments of the present invention will be described with reference to the attached drawings. FIG. 1 is a diagram that schematically illustrates a fluorescence detecting apparatus 1 according to a preferred embodiment of the present invention. The fluorescence detecting apparatus 1 is an immunoanalysis apparatus that utilizes surface plasmon resonance. When analysis is performed by the fluorescence detecting apparatus 1, a sample container CB, a nozzle tip NT which is used to extract samples and reagents, and an analysis chip 10, I which a reagent cell and a micro flow channel are formed. Note that the nozzle tip NT and the analysis chip 10 are disposable and are to be discarded after a single use. The fluorescence detecting apparatus 1 performs quantitative or qualitative analysis of a detection target substance within a sample.

The fluorescence detecting apparatus 1 is equipped with: a sample processing means 20; a light irradiating means 30; a fluorescence detecting means 40; and a data analyzing means 50. The sample processing means 20 employs the nozzle tip NT to extract a sample from the sample container CB, and generates a sample solution by mixing and agitating the extracted sample and a reagent.

Figure 3:
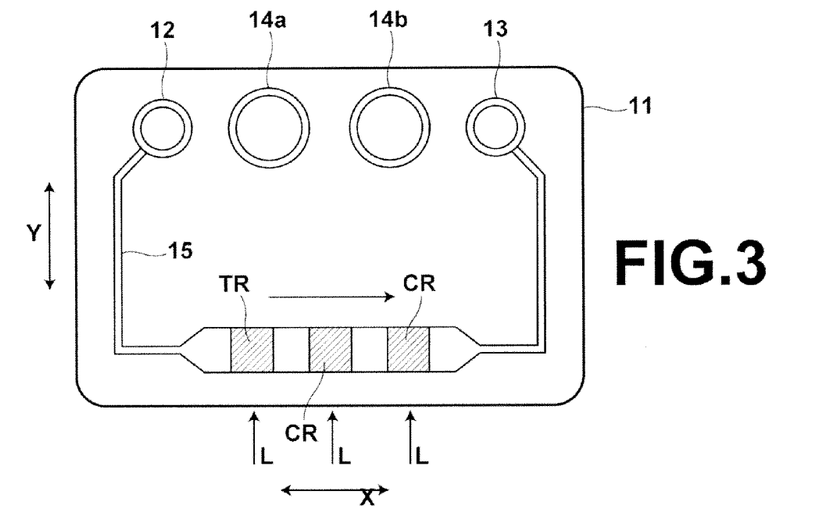
FIG. 3 is a diagram that schematically illustrates an analysis chip employed by the fluorescence detecting apparatus of FIG. 1.

FIG. 3 is a diagram that schematically illustrates an example of the analysis chip 10. The analysis chip 10 is of a configuration in which an injection opening 12, a discharge opening 13, sample cells 14a and 14b, and a flow channel 15 are formed in a main body 11 formed by a transparent resin. The injection opening 12 communicates with the discharge opening 13 via the flow channel 15. The sample is injected into the flow channel 15 through the injection opening 12, flows through the flow channel 15, and is discharged through the discharge opening 13 by negative pressure being applied to the discharge opening 13. The sample cells 14a and 14b are containers that contain fluorescent reagents (secondary antibodies) to be mixed with the sample within the sample container CB. Note that the openings of the sample cells 14a and 14b are sealed by a sealing member, and the sealing members are perforated when the sample and the fluorescent reagents are to be mixed.

A test region TR for detecting the detection target substance within the sample is formed within the flow channel 15. Two control regions CR are formed in the flow channel 15 downstream form the test region TR. First antibodies are immobilized on the test region TR, and capture labeled antibodies by the so called sandwich method. In addition, reference antibodies are immobilized onto the control regions CR, and the reference antibodies capture fluorescent substances by the sample solution being caused to flow over the control regions CR. Note that two control regions CR include a negative type control region CR, for detecting nonspecific adsorption, and a positive type control region CR, for detecting differences in reactivity due to differences among samples.

Figure 4:
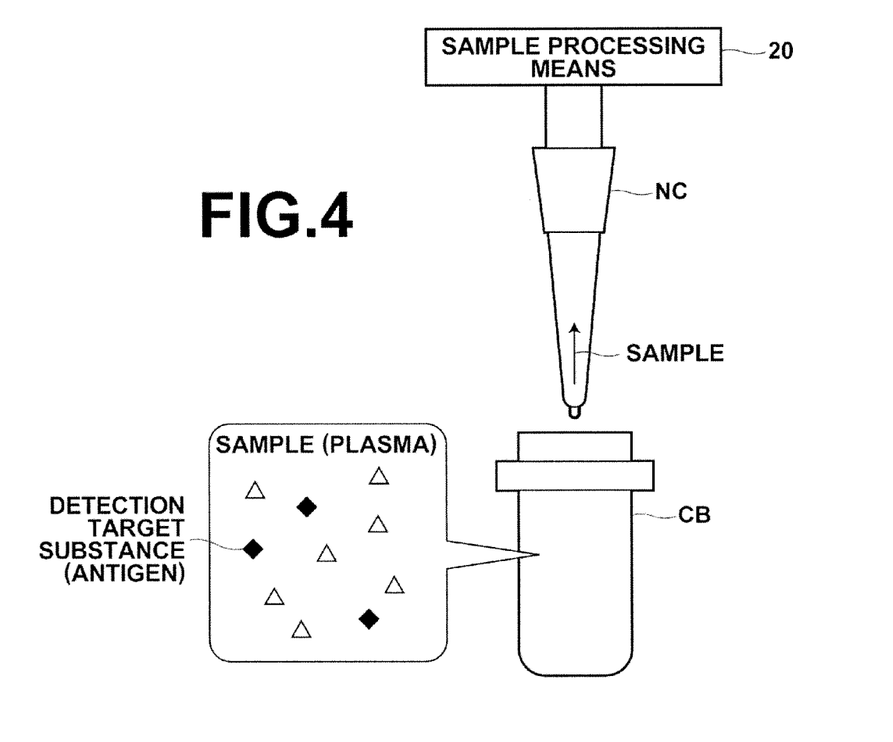
FIG. 4 is a diagram that schematically illustrates a state in which a sample processing means of FIG. 2 employs a nozzle chip to extract a sample from a sample container.
Figure 5:
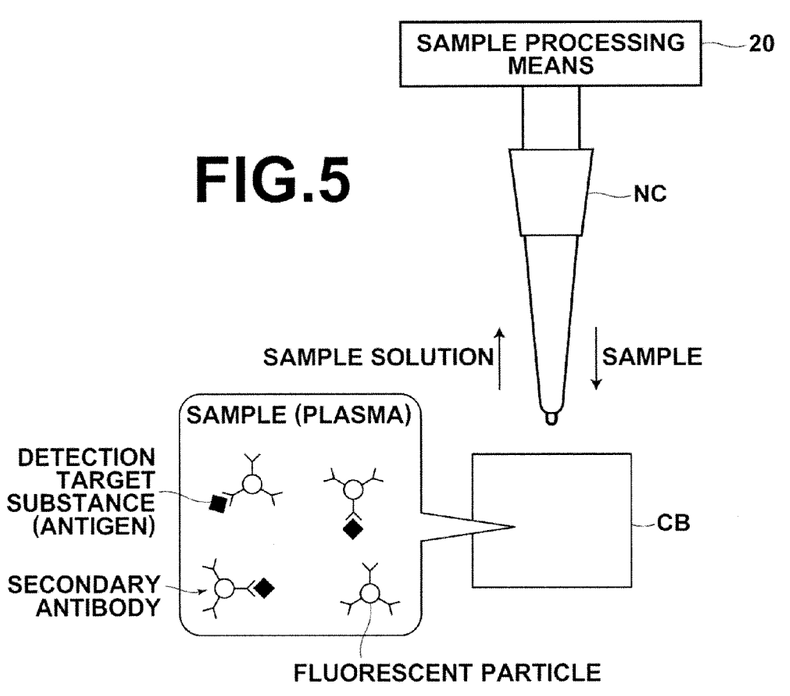
FIG. 5 is a diagram that schematically illustrates a state in which the sample processing means of FIG. 2 injects the sample from the nozzle chip to a reagent cell and agitates the sample.

When initiation of analysis is instructed, the sample processing means 20 employs the nozzle tip NT to suction a sample form the sample container CB, as illustrated in FIG. 4. Thereafter, the sample processing means perforates the sealing member of the sample cell 14a, mixes and agitates the sample with the reagent in the sample cell 14a, then suctions the sample solution again with the nozzle tip NT. This operation is repeated with respect to sample cell 14b as well. Thereby, a sample solution that includes detection target substance A (antigens A) contained in the sample, the surfaces of which are modified by secondary antibodies B2, which is a secondary binding substance that specifically binds with the antigens A and is contained in the reagent, is produced. Then, the sample processing means 20 places the nozzle tip NT having the sample solution therein above the injection opening 12. The sample solution within the nozzle tip NT is caused to flow into the flow channel by negative pressure applied from the discharge opening 13.

Note that a case has been described in which the sample processing means 20 supplies the sample solution, in which the sample and the reagent are mixed, into the flow channel 15. Alternatively, the reagent may be provided in the flow channel 15 in advance, and the sample processing means 20 may simply cause the sample to flow into the flow channel 15 through the injection opening.

Figure 6:
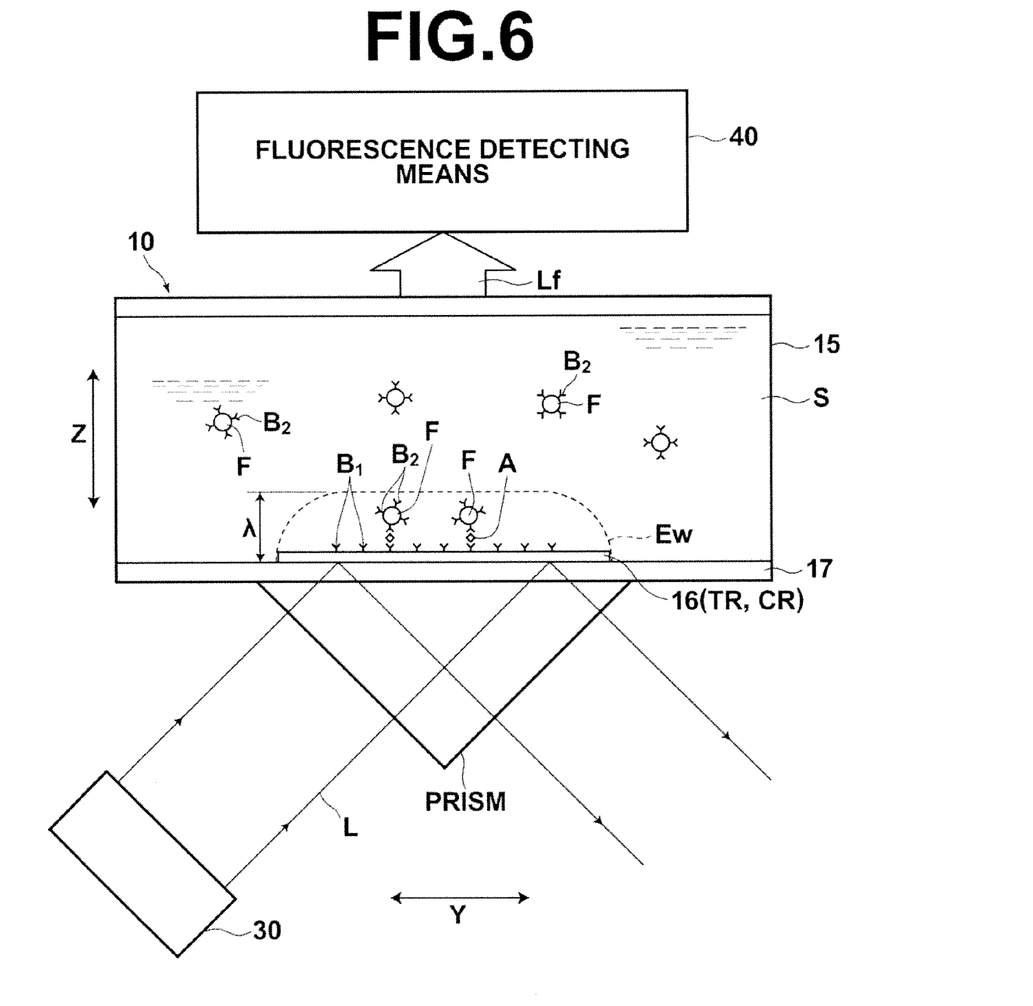
FIG. 6 is a diagram that schematically illustrates an example of a light irradiating means and an example of a fluorescence detecting means of FIG. 2.

FIG. 6 is a diagram that schematically illustrates an example of the light irradiating means 30 and an example of the fluorescence detecting means 40. Note that the description given with reference to FIG. 6 will focus on the test region T. However, an excitation light beam L is irradiated onto the control regions CR in the same manner as in the following description. The light irradiating means 30 of FIG. 2 irradiates the excitation light beam L onto the interface between a dielectric plate 17 and a metal film 16 of the test region TR at an incident angle that satisfies conditions for total reflection, from the underside of the analysis chip 10 via a prism. The fluorescence detecting means 40 is constituted by photodiodes, CCD's, COMOS's or the like. The fluorescence detecting means 40 detects fluorescence generated at the test region TR by irradiation of the excitation light beam L by the light irradiating means 30 as fluorescence signals FS.

The light irradiating means 30 irradiates the excitation light beam L onto the interface between the dielectric plate 17 and the metal film 16 at a specific incident angle greater than or equal to a total reflection angle, causing evanescent waves Ew to seep out into the sample S on the metal film 16. The evanescent waves Ew excite surface plasmon within the metal film 16. The surface plasmon generates an electric field distribution on the surface of the metal film 16, to form an electric field enhancing region. A fluorescent labeling substance F which is bound to the metal film 16 is excited by the evanescent waves Ew and generates amplified fluorescence.

Figure 2:
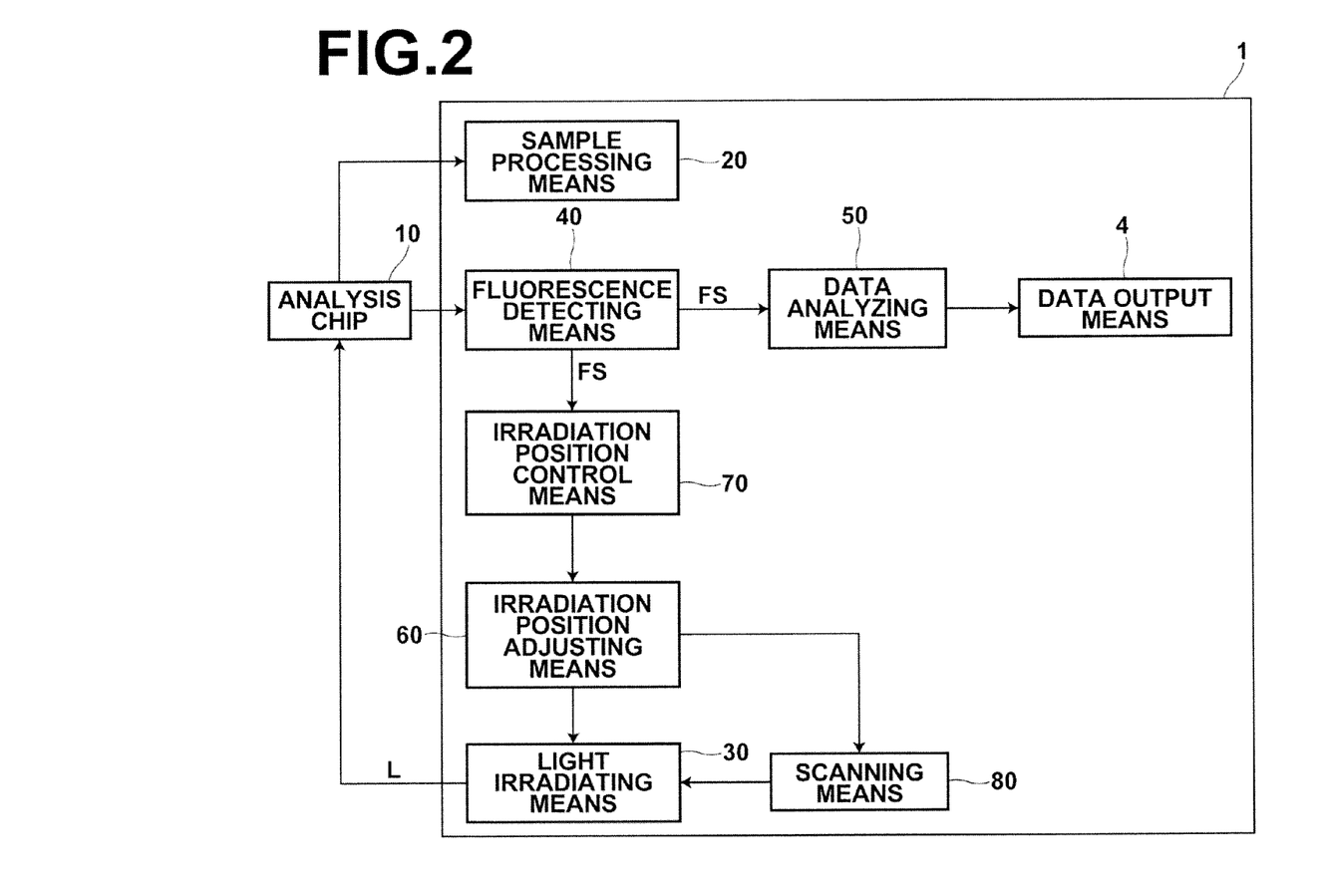
FIG. 2 is a block diagram that illustrates the fluorescence detecting apparatus according to the preferred embodiment of the present invention.
Figure 7:
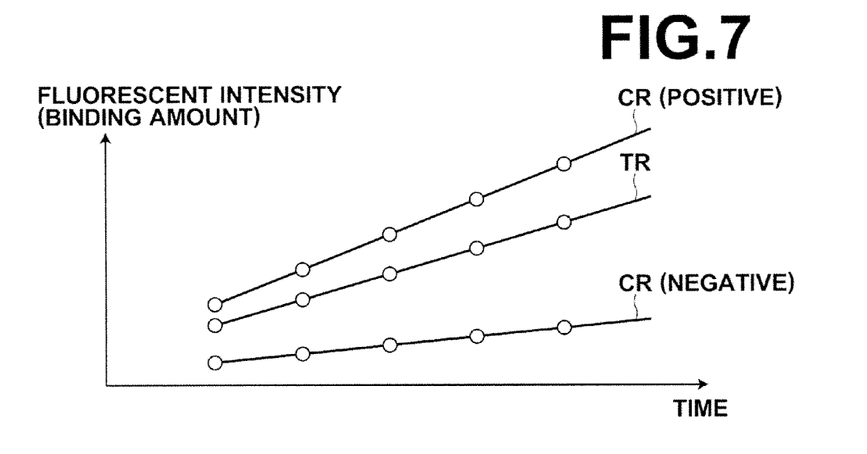
FIG. 7 is a graph that illustrates the manner in which quantitative or qualitative analysis is performed by a data analyzing means of FIG. 2 using the rate method.

The data analyzing means 50 of FIG. 2 analyzes the detection target substance based on changes in the fluorescence signals FS detected by the fluorescence detecting means 40 over time. Specifically, the intensity of fluorescence changes according to the amount of the fluorescent labeling substance F which is bound to the metal film 16. Therefore, the intensity of fluorescence changes over time as illustrated in FIG. 7. The data analyzing means 50 obtains a plurality of fluorescence signals over a predetermined period of time (5 minutes, for example) at a predetermined sampling interval (5 second intervals, for example), and performs quantitative analysis of the detection target substance within the sample by analyzing the change in the intensity of fluorescence over time (the rate method). The analysis results are output from a data output means 4, such as a monitor, a printer, or the like.

The fluorescence detecting apparatus 1 has a function of adjusting the irradiation position RR of the excitation light beam L to adjust for individual differences among analysis chips 10 prior to performing the analysis of the detection target described above. That is, the analysis chips are disposable, and a different analysis chip 10 is employed for each analysis operation. There are cases in which the shapes and sizes of the analysis chips, and the positions at which the test region TR and the control regions CR are formed therein differ due to manufacturing errors. In these cases, the areas of the test region TR and the control regions CR which are irradiated by the excitation light beam L will differ due to individual differences among the analysis chips 10. The intensity of the aforementioned electric field enhancing field (evanescent waves) differs according to the amount of irradiated excitation light beam. Therefore, if the irradiation areas are different, the intensity of the electric field enhancing field and the amount of fluorescence amplified thereby will also differ. As a result, there is a problem that the intensity of fluorescence will fluctuate due to the individual differences, and accuracy of analysis will deteriorate. Therefore, the fluorescence detecting apparatus 1 has a function that automatically adjusts the irradiation position of the excitation light beam L to accommodate individual differences among analysis chips 10.

Figure 8:
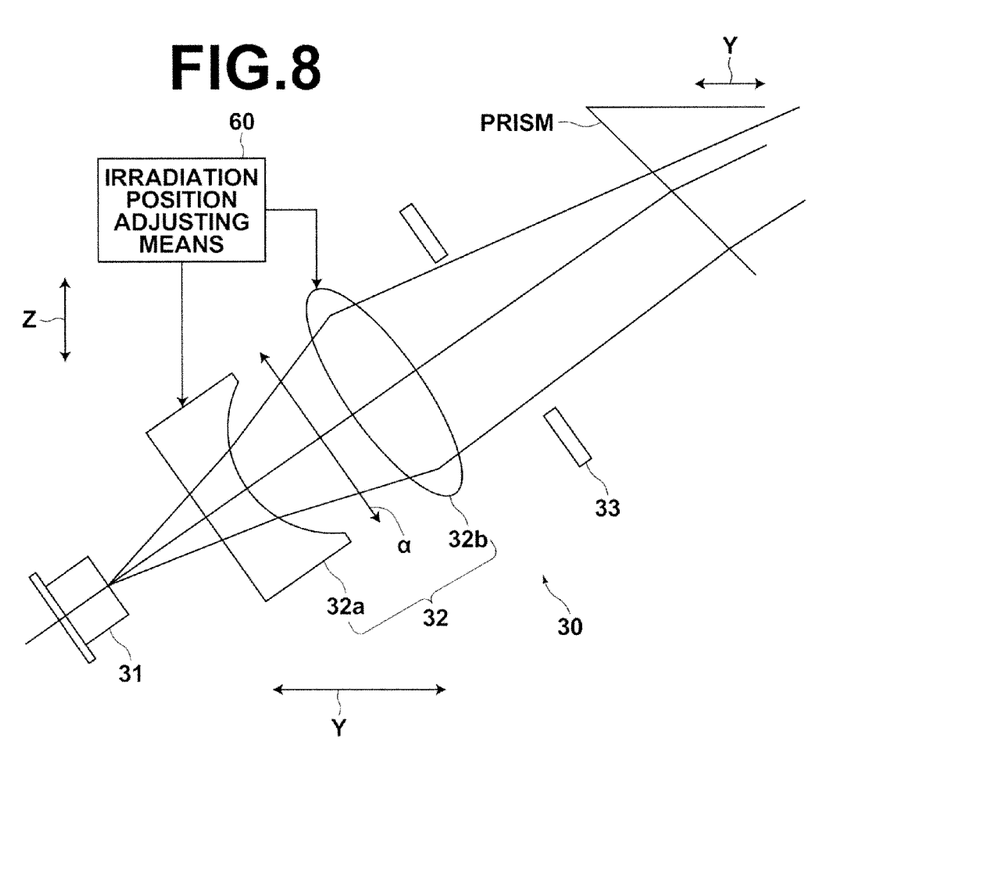
FIG. 8 is a diagram that schematically illustrates an example of an irradiation position adjusting means of FIG. 2.
Figure 9:
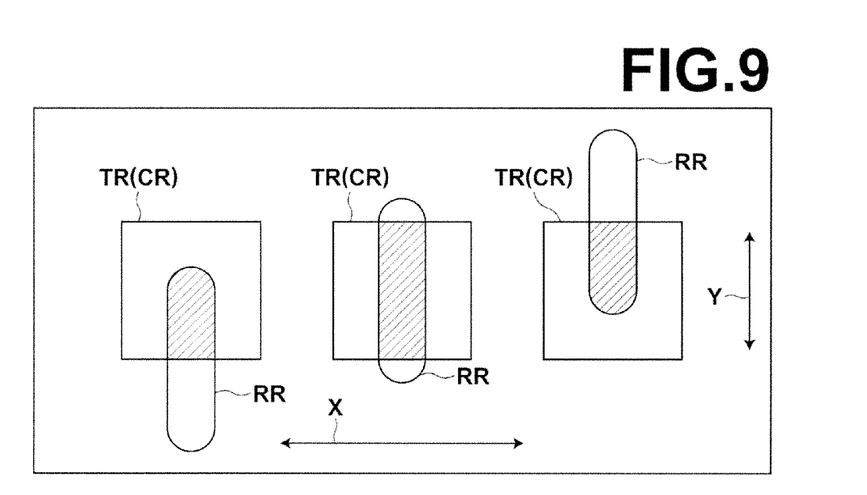
FIG. 9 is a diagram that schematically illustrates the manner in which the irradiation position of an excitation light beam is moved in the direction indicated by arrow Y by the irradiation position adjusting means of FIG. 8.

Specifically, the fluorescence detecting apparatus 1 of FIG. 2 is equipped with an irradiation position adjusting means 60 and an irradiation position control means 70. The irradiation position adjusting means 60 adjusts the irradiation position RR of the excitation light beam L with respect to the test region TR. FIG. 8 is a diagram that schematically illustrates an example of the light irradiating means 30 and an example of the irradiation position adjusting means 60. In FIG. 8, the light irradiating means 30 is equipped with: a light source 31; an optical system 32 constituted by a concave lens 32a and a convex lens 32b; and an aperture 33. The excitation light beam L emitted by the light source 31 is focused by the optical system 32, and enters the prism via the aperture 33. The irradiation position adjusting means 60 adjusts the irradiation position RR of the excitation light beam L in a direction (indicated by arrow Y) substantially parallel to the plane of the test region and substantially parallel to the incident surface of the excitation light beam L, by moving the position of the optical system 32 in a direction (indicated by arrow α) substantially perpendicular to the optical axis thereof and substantially parallel to the incident surface of the excitation light beam L. Note that a case has been described in which the optical system 32 focuses the excitation light beam L. Alternatively, the optical system 32 may collimate or spread the excitation light beam L.

Figure 10:
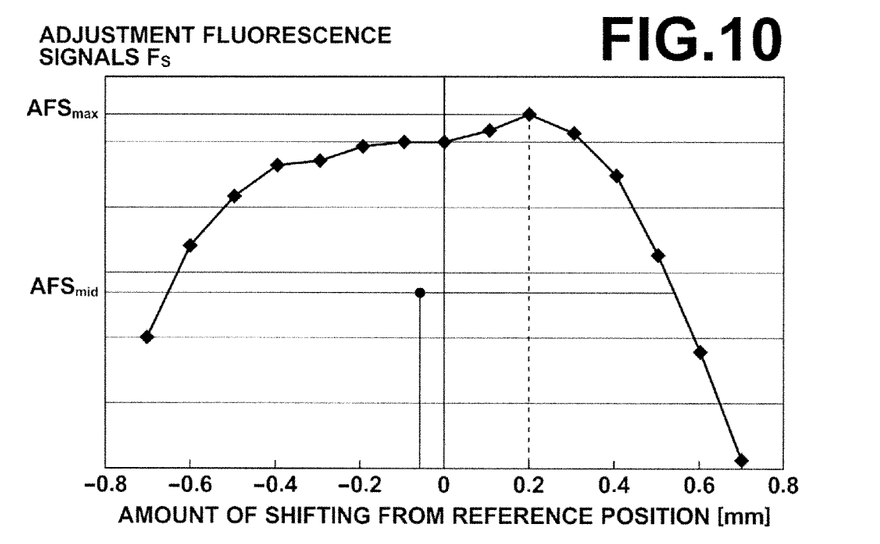
FIG. 10 is a graph that illustrates an example of a relationship between amounts of shifting in irradiation positions and intensities of adjustment fluorescence signals.

The irradiation position control means 70 drives the irradiation position adjusting means 60 to cause the excitation light beam L to be irradiated onto the test region TR while shifting the irradiation position RR. Then, the irradiation position control means 70 determines the irradiation position RR of the excitation light beam with respect to the test region TR during analysis of the detection target substance, based on a plurality of adjustment fluorescence signals AFS detected by the fluorescence detecting means 40. Specifically, the irradiation position control means 70 controls the irradiation position adjusting means 60 such that the irradiation position RR of the excitation light beam L is shifted within a scanning range of 1.5 mm in 0.1 mm increments. Thereby, a plurality of adjustment fluorescence signals AFS as illustrated in FIG. 10 are detected for each different irradiation position RR by the fluorescence detecting means 40. Note that the shift amount 0 of FIG. 10 indicates an initial position which is set in advance.

The irradiation position control means 70 detects a maximum adjustment fluorescence signal $AFS_{max}$ from among the plurality of adjustment fluorescence signals AFS. Then, the irradiation position control means 70 determines the irradiation position RR at which the maximum adjustment fluorescence signal $AFS_{max}$ was obtained as the optimal irradiation position RR for performing the aforementioned analysis. Therefore, the irradiation position control means 70 controls the irradiation position adjusting means 60 to perform the analysis at this irradiation position RR. Alternatively, the irradiation position control means 70 may control the irradiation position adjusting means 60 to perform the analysis at an irradiation position RR at the center of a scanning range in which the detected adjustment fluorescence signals AFS exceed 50% of the maximum adjustment fluorescence signal $AFS_{max}$. The operation for adjusting the irradiation position RR is performed each time that the analysis chip 10 is exchanged. Thereby, deterioration of analysis accuracy due to individual differences among analysis chips 10 can be prevented.

Figure 11:
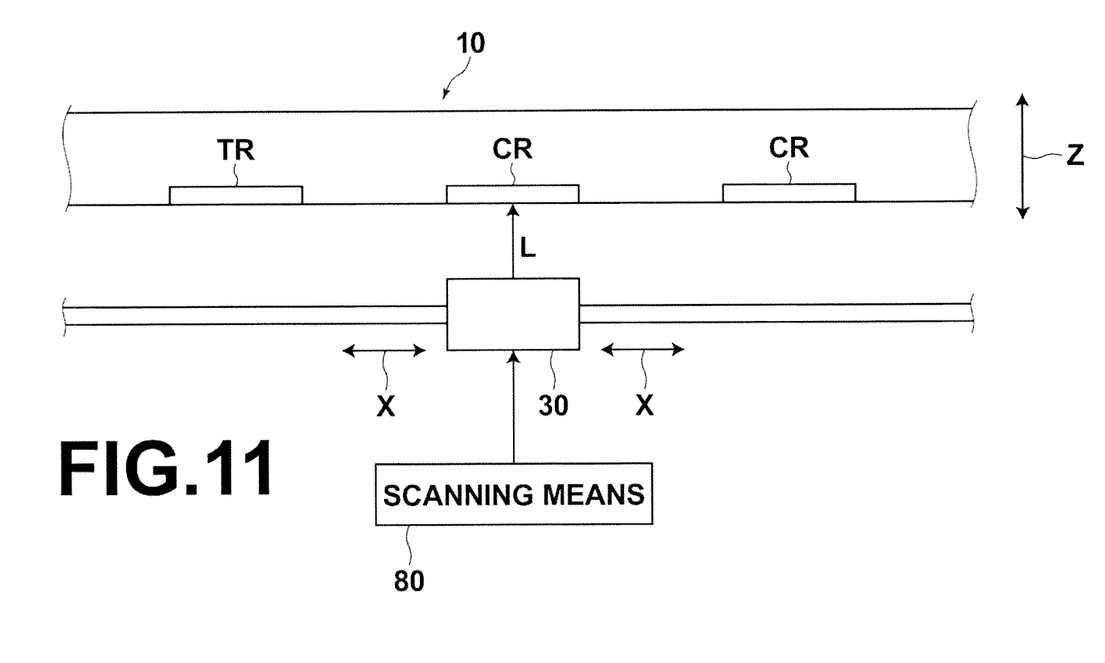
FIG. 11 is a diagram that schematically illustrates an example of a scanning means of FIG. 2.

As described previously, the two control regions CR are provided in the sensor chip 10 in addition to the test region TR. Fluorescence detection is performed at these control regions CR as well. Irradiation of the excitation light beam L onto the test region TR and the control regions CR is performed by scanning the light irradiating means 30. FIG. 11 is a diagram that schematically illustrates an example of a scanning means 80. The scanning means 80 moves the light irradiating means 30 in the direction (indicated by arrow X) along which the flow channel is formed. The scanning means 80 causes the light irradiating means 30 to move reciprocally between the test region TR and the control regions CR in 5 second intervals, for example.

Figure 12:
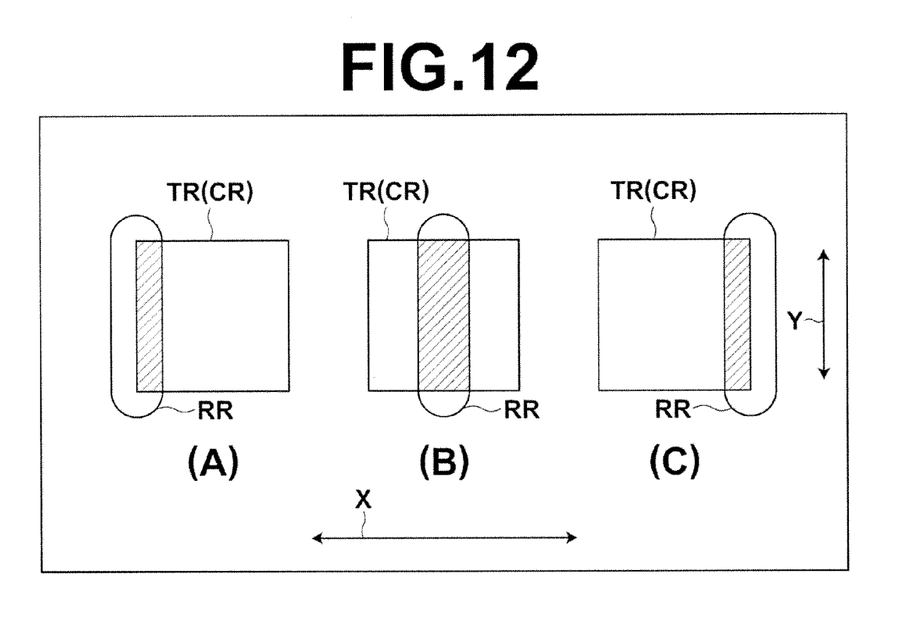
FIG. 12 is a diagram that schematically illustrates the manner in which the irradiation position of an excitation light beam is moved in the direction indicated by arrow Y by the scanning means of FIG. 11.

There are cases in which positional shifting occurs not only in the Y direction but also in the X direction, due to individual differences among analysis chips 10. For this reason, the irradiation position control means 70 adjusts the irradiation position RR in the X direction as well, using the scanning means 80. Specifically, the irradiation position control means 70 drives the scanning means 80 to irradiate the excitation light beam L onto the test region TR while shifting the irradiation position RR as illustrated in FIG. 12. The fluorescence detecting means 40 detects a plurality of adjustment fluorescence signals AFS for each irradiation position RR. The irradiation position control means 70 determines the irradiation position of the excitation light beam L in the X direction in the same manner as that which is employed to determine the irradiation position in the Y direction described above.

Note that a case has been described in which the scanning means 80 is employed to adjust the irradiation position RR in the X direction, and the irradiation position adjusting means 60 is employed to adjust the irradiation position RR in the Y direction. However, the irradiation position adjusting means 60 may be employed to adjust the irradiation position RR in the X direction as well. In this case, the irradiation position adjusting means 60 adjusts the irradiation position RR by moving the optical system 32 in the direction indicated by arrow α and a direction perpendicular thereto. A case has been described in which the irradiation position RR is adjusted with respect to the test region TR with reference to FIG. 8. In addition, adjustment of the irradiation position RR with respect to the control regions CR is performed as well.

Further, a case in which the light irradiating means 30 is moved in the direction of arrow X has been described. The fluorescence detecting means 40 may also been moved in a synchronized manner with the movement of the light irradiation means 30. Alternatively, light detecting portions may be provided for each of the test region TR and the control regions CR.

Figure 13:
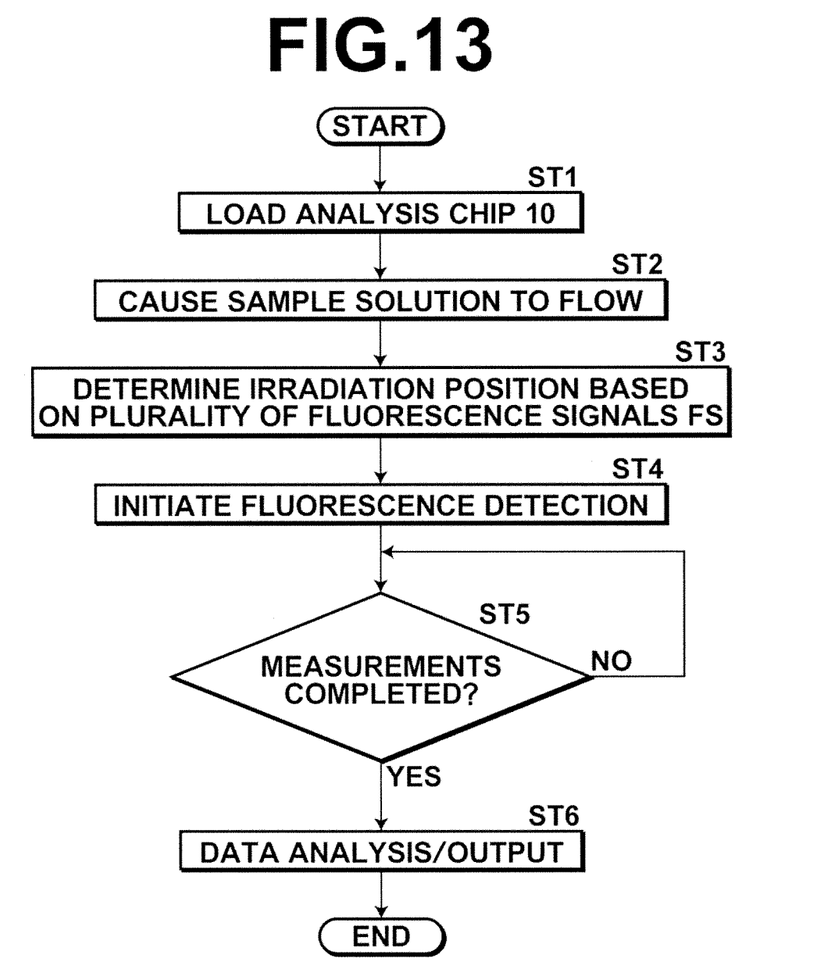
FIG. 13 is a flow chart that illustrates the steps of a fluorescence detecting method according to a preferred embodiment of the present invention.

FIG. 13 is a flow chart that illustrates the steps of a fluorescence detecting method according to a preferred embodiment of the present invention. The fluorescence detecting method of the present invention will be described with reference to FIG. 13. First, an analysis chip 10, a sample container CB, and a nozzle tip NT are loaded into the fluorescence detecting apparatus 1 (step ST1). Then, the sample processing means 20 produces a sample solution in which the sample and a reagent are mixed, and this sample solution is caused to flow into the flow channel of the analysis chip 10 (step ST2).

The process is placed on standby until a sufficient amount of time elapses for fluorescence of intensities sufficient to adjust irradiation positions are generated at the test region TR and the control regions CR.

Next, the irradiation positions RR with respect to the test region TR and the control regions CR are adjusted (step ST3). Specifically, adjustment fluorescence signals AFS are obtained while moving the irradiation position RR of the excitation light beam L in a direction (indicated by arrow Y) perpendicular to the direction that the flow channel extends in. Then, an optimal irradiation position RR in the Y direction is determined and recorded, based on the adjustment fluorescence signals AFS. Similarly, adjustment fluorescence signals AFS are obtained while moving the irradiation position RR of the excitation light beam L by the scanning means 80 in a direction (indicated by arrow X) that the flow channel extends in. Then, an optimal irradiation position RR in the X direction is determined and recorded, based on the adjustment fluorescence signals AFS.

The adjustments are performed at speeds sufficiently high enough to ignore changes in fluorescent signals due to reactions. In addition, in the case that fluorescence signals of intensities necessary to perform adjustment cannot be obtained at the negative control region, at which reactions do not practically occur, adjustment values obtained at the positive control region can be substituted.

After the irradiation position RR of the excitation light beam L is determined, irradiation of the excitation light beam L for quantitative analysis of the detection target substance is executed (step ST4). At this time, the light irradiating means 30 is scanned in the direction of arrow X to irradiate the excitation light beam L onto the test region TR and the control regions CR. Then, the fluorescence signals FS are obtained within a predetermined period of time at predetermined sampling intervals, for example (step ST5, refer to FIG. 7). Thereafter, the data analyzing means 50 performs quantitative analysis using the rate method, and the results of analysis are printed out or displayed on a screen (step ST6).

The embodiment described above employs the analysis chip 10 having the test region TR, for capturing a detection target substance included in a sample solution, within a flow channel through which the sample solution is caused to flow, irradiates an excitation light beam onto the test region, and detects fluorescence generated at the test region, to analyze the detection targets substance. A plurality of adjustment fluorescence signals AFS are detected as the excitation light beam L is irradiated onto the test region while shifting the irradiation position RR thereof. The irradiation position RR of the excitation light beam with respect to the test region TR during analysis of the detection target substance is determined, based on the plurality of detected adjustment fluorescence signals AFS. The detection target substance is analyzed by irradiating the excitation light beam L onto the determined irradiation position RR and detecting fluorescence. Thereby, shifts in the irradiation position of the excitation light beam with respect to test regions TR due to individual differences among analysis chips 10 are automatically adjusted for. This enables analysis to be performed under the same excitation light beam irradiation conditions for all analysis chips 10. Therefore, deterioration in the accuracy of analysis due to individual differences among analysis chips 10 can be prevented.

In the case that that the irradiation position control means 70 determines an irradiation position at which the adjustment fluorescence signal $AFS_{max}$ is the greatest from among the plurality of adjustment fluorescence signals AFS as the irradiation position RR during an analysis operation as illustrated in FIG. 10, an irradiation position RR that yields accurate analysis results can be determined. Alternatively, in the case that the irradiation position control means 70 specifies a range of irradiation positions in which adjustment fluorescent signals of an intensity which is a predetermined percentage of the greatest adjustment fluorescence signal are obtained, and determines a midpoint position within the specified range of irradiation positions as the irradiation position during an analysis operation, an irradiation position that yields accurate analysis results can be determined.

Further, the analysis chip is equipped with control regions CR that generate fluorescence when the sample solution passes therethrough due to irradiation of the excitation light beam, downstream of the test region TR, and scanning means for scanning the light irradiation means between the test region and the control region when irradiating the excitation light beam to analyze the detection target substance is provided in the fluorescence detecting apparatus 1 as illustrated in FIG. 11 and FIG. 12. In this case, the necessity to provide separate light irradiating means for each of the test region TR and the control regions CR is obviated, and the structure of the apparatus may be simplified.

Further, the fluorescence detecting means 40 detects a plurality of adjustment fluorescence signals AFS while shifting the irradiation position RR of the excitation light beam L with respect to the test region TR or the control regions CR, by performing scanning by the scanning means. The irradiation position control means 70 determines the irradiation position RR of the light irradiating means 30 in the scanning direction (indicated by arrow X) based on the plurality of detected adjustment fluorescence signals AFS. Therefore, analysis can be performed at an optimal irradiation position, regardless of positional fluctuations of the test region TR in the scanning direction (indicated by arrow X) due to individual differences among analysis chips 10.

As illustrated in FIG. 6, the test region TR is equipped with the dielectric plate 17 and the metal film 16 such that an electric field enhancing field is generated on the test region TR by irradiation of the excitation light beam L. In this case, the intensity of the electric field enhancing field being different for each analysis chip 10 can be prevented, and accurate analysis of the detection target substance is enabled.

The present invention is not limited to the embodiments described above. For example, a case has been described in which adjustment of the irradiation position RR is performed in the direction (indicated by arrow X) along the flow channel. Alternatively, the adjustment of the irradiation position RR may be practically performed by selecting a fluorescence signal FS in the X direction may be selected as that which is employed to perform analysis. Specifically, the fluorescence detecting means 40 obtains a plurality of fluorescence signals FS from the scanning regions in the vicinities of the test region TR and the control regions CR during an analysis operation. Then, the data analyzing means 50 may perform data analysis after selecting the greatest fluorescence signal FS from among the plurality of fluorescence signals. In this case as well, deterioration in the accuracy of analysis due to positional shifts in the direction (the direction indicated by arrow X) of the flow channel caused by individual differences among analysis chips 10 can be prevented.

In addition, the embodiments have been described as cases in which the rate method, in which fluorescence signals change over type according to reactions, is employed. However, deterioration of the accuracy of analysis can also be prevented in analysis that employs the endpoint method, in which steady fluorescence signals are measured after reactions are stopped by cleansing.

What is claimed is:

1. A fluorescence detecting apparatus that employs an analysis chip comprising a test region, for capturing a detection target substance included in a sample solution, within a flow channel through which the sample solution is caused to flow, irradiates an excitation light beam onto the test region, and detects fluorescence generated at the test region, to analyze the detection targets substance, comprising:
   light irradiating means, for emitting the excitation light beam onto the test region;
   fluorescence detecting means, for detecting the fluorescence generated at the test region due to the irradiation of the excitation light beam;
   irradiation position adjusting means, for adjusting the irradiation position of the excitation light beam with respect to the test region; and
   irradiation position control means, for determining the irradiation position of the excitation light beam with respect to the test region during analysis of the detection target substance, based on a plurality of adjustment fluorescence signals detected by the fluorescence detecting means when the irradiation position adjusting means is driven to irradiate the excitation light beam onto the test region while shifting the irradiation position of the excitation light beam.

2. A fluorescence detecting apparatus as defined in claim 1, wherein:
   the light irradiating means comprises a light source for emitting the excitation light beam, and an optical system for causing the excitation light beam emitted by the light source to enter the test region; and
   the irradiation position adjusting means adjusts the irradiation position of the excitation light beam in a direction substantially parallel to the plane of the test region and substantially parallel to the incident surface of the excitation light beam, by moving the position of the optical system in a direction substantially perpendicular to the optical axis of the optical system and substantially parallel to the incident surface of the excitation light beam.

3. A fluorescence detecting apparatus as defined in claim 1, wherein:
   the irradiation position control means determines an irradiation position at which the adjustment fluorescence signal comprises a greatest from among the plurality of adjustment fluorescence signals as the irradiation position during an analysis operation.

4. A fluorescence detecting apparatus as defined in claim 1, wherein:
   the irradiation position control means detects the greatest adjustment fluorescence signal from among the plurality of adjustment fluorescence signals, specifies a range of irradiation positions in which adjustment fluorescent signals of an intensity which comprises a predetermined percentage of the greatest adjustment fluorescence signal are obtained, and determines a midpoint position within the specified range of irradiation positions as the irradiation position during an analysis operation.

5. A fluorescence detecting apparatus as defined in claim 1, wherein:
   the irradiation position control means performs adjustment of the irradiation position each time that the analysis chip is exchanged.

6. A fluorescence detecting apparatus as defined in claim 1, wherein:
   the analysis chip comprises a control region that generates fluorescence when the sample solution passes therethrough due to irradiation of the excitation light beam, downstream of the test region; and
   the fluorescence detecting apparatus further comprises a scanning means for scanning the light irradiation means between the test region and the control region when irradiating the excitation light beam to analyze the detection target substance.

7. A fluorescence detecting apparatus as defined in claim 6, wherein:
   the fluorescence detecting means detects the plurality of adjustment fluorescence signals while shifting the irradiation position of the excitation light beam with respect to the test region by scanning performed by the scanning means; and
   the position control means determines the irradiation position of the excitation light beam in a scanning direction based on the plurality of adjustment fluorescence signals, and determines the irradiation position of the excitation light beam in a direction perpendicular to the flow channel by the irradiation position adjusting means.

8. A fluorescence detecting apparatus as defined in claim 7, wherein the irradiation position of the excitation light beam is shifted within a scanning range of 1.5 mm to 0.1 mm increments.

9. A fluorescence detecting apparatus as defined in claim 7, wherein the irradiation position control means determines an adjustment fluorescence signal of the plurality of adjustment fluorescence signals which has a greatest value.

10. A fluorescence detecting apparatus as defined in claim 9, wherein the irradiation position control means determines the irradiation position corresponding to the adjustment fluorescence signal having the greatest value.

11. A fluorescence detecting apparatus as defined in claim 6, wherein the irradiation position adjusting means adjusts the irradiation position of the excitation light beam with respect to the control region.

12. A fluorescence detecting apparatus as defined in claim 6, wherein the irradiation position control means determines the irradiation position of the excitation light beam with respect to the control region during analysis of the detection target substance, based on a plurality of adjustment fluorescence signals detected by the fluorescence detecting means when the irradiation position adjusting means is driven to irradiate the excitation light beam onto the control region while shifting the irradiation position of the excitation light beam.

13. A fluorescence detecting apparatus as defined in claim 1, wherein:
   the test region comprises a dielectric plate and a metal film such that an electric field enhancing field is generated by irradiation of the excitation light beam, and the detection target substance generates fluorescence by being excited by the electric field enhancing field.

14. A fluorescence detecting apparatus as defined in claim 1, wherein:

the sample liquid comprises the detection target substance and fluorescent labels being mixed, and the test region captures the detection target substance which has bound to the fluorescent labels.

15. A fluorescence detecting apparatus as defined in claim 1, wherein the light irradiating means comprises a light source for emitting the excitation light beam, and an optical system for causing the excitation light beam emitted by the light source to enter the test region, and wherein the irradiation position adjusting means adjusts the irradiation position of the excitation light beam in a direction substantially parallel to the plane of the test region and substantially parallel to the incident surface of the excitation light beam, by moving the position of the optical system in a first direction substantially perpendicular to the optical axis of the optical system and in a second direction substantially perpendicular to the first direction.

16. A fluorescence detecting method that employs an analysis chip comprising a test region within a flow channel through which a sample solution is caused to flow, for capturing a detection target substance included in the sample solution, irradiates an excitation light beam onto the test region, and detects fluorescence generated at the test region, to analyze the detection targets substance, comprising:

emitting the excitation light beam onto the test region;

detecting the fluorescence generated at the test region due to the irradiation of the excitation light beam;

adjusting the irradiation position of the excitation light beam with respect to the test region; and determining the irradiation position of the excitation light beam with respect to the test region during analysis of the detection target substance, based on a plurality of detected adjustment fluorescence signals when the excitation light beam is irradiated onto the test region while shifting the irradiation position of the excitation light beam.

* * * * *